US011083626B2

(12) United States Patent
Seiler, Sr. et al.

(10) Patent No.: US 11,083,626 B2
(45) Date of Patent: Aug. 10, 2021

(54) SYSTEM FOR FRAGMENTING AN EYE LENS NUCLEUS

(71) Applicant: IROC Services AG, Zug (CH)

(72) Inventors: Theo Seiler, Sr., Zurich (CH); Theo Guenther Seiler, Jr., Zurich (CH); Stefan Seiler, Zurich (CH)

(73) Assignee: IROC Services AG, Zug (CH)

( * ) Notice: Subject to any disclaimer, the term of this patent is extended or adjusted under 35 U.S.C. 154(b) by 65 days.

(21) Appl. No.: 15/799,822

(22) Filed: Oct. 31, 2017

(65) Prior Publication Data

US 2018/0125714 A1    May 10, 2018

(30) Foreign Application Priority Data

Nov. 4, 2016  (EP) .................................... 16197287

(51) Int. Cl.
*A61F 9/008*       (2006.01)
*A61F 9/007*       (2006.01)
(Continued)

(52) U.S. Cl.
CPC .......... *A61F 9/00825* (2013.01); *A61B 18/20* (2013.01); *A61F 9/00736* (2013.01);
(Continued)

(58) Field of Classification Search
None
See application file for complete search history.

(56) References Cited

U.S. PATENT DOCUMENTS

2012/0302862 A1\* 11/2012 Yun ..................... A61B 5/0068
                                                        600/398
2014/0316388 A1\* 10/2014 Hipsley ............... A61F 9/00802
                                                         606/4
(Continued)

FOREIGN PATENT DOCUMENTS

DE    102013211854 A1    12/2014
WO    2016131815 A1    8/2016
WO    2016168759 A1    10/2016

OTHER PUBLICATIONS

Sebastian Besner, Giuliano Scarcelli, Roberto Pineda, Soek-Hyun Yun, "In Vivo Brillouin Analysis of the Aging Crystalline Lens", Investigative Ophthalmology & Visual Science, Oct. 2016, pp. 5093-5100, vol. 57, No. 13.
(Continued)

*Primary Examiner* — Michael W Kahelin
*Assistant Examiner* — Elizabeth K So
(74) *Attorney, Agent, or Firm* — Straub & Straub; Michael P. Straub; Stephen T. Straub

(57) ABSTRACT

A system for fragmenting an eye lens nucleus has a first laser radiation source 30, configured to irradiate the eye lens nucleus with first radiation 32 suitable for Brillouin spectroscopy; an apparatus 36 for performing Brillouin spectroscopy with radiation scattered back from the eye lens nucleus in order to acquire Brillouin scattering measured data; a processing unit 50 in or from which correlations between Brillouin scattering measured data and parameters of a second radiation 52 suitable for fragmenting the eye lens nucleus 12 are stored or derived; and a second laser radiation source 44 having radiation guiding means 40, configured to irradiate the eye lens nucleus 12 with the second radiation with the parameters correlated with the Brillouin scattering
(Continued)

measured data of the irradiated eye lens nucleus 12, in order to fragment the eye lens nucleus.

<p align="center">4 Claims, 1 Drawing Sheet</p>

(51) Int. Cl.
*A61B 18/20* (2006.01)
*A61B 18/00* (2006.01)
*A61N 7/00* (2006.01)

(52) U.S. Cl.
CPC ............... *A61B 2018/00601* (2013.01); *A61F 2009/0087* (2013.01); *A61F 2009/00887* (2013.01); *A61F 2009/00897* (2013.01); *A61N 7/00* (2013.01)

(56) References Cited

U.S. PATENT DOCUMENTS

2016/0151202 A1* 6/2016 Scarcelli ................. A61F 9/008
606/5
2016/0220110 A1 8/2016 Volger et al.

OTHER PUBLICATIONS

Stephan Reiss, Gerolf Burau, Oliver Stachs, Rudolf Guthoff, Heinrich Stolz, "Spatially resolved Brillouin spectroscopy to determine the rheological properties of the eye lens", Biomedical Optics Express, Aug. 1, 2011, pp. 2144-2159, vol. 2, No. 8.
European Patent Office, European Search Report From EP Application 161972872, dated May 10, 2017, pp. 1-6.

* cited by examiner

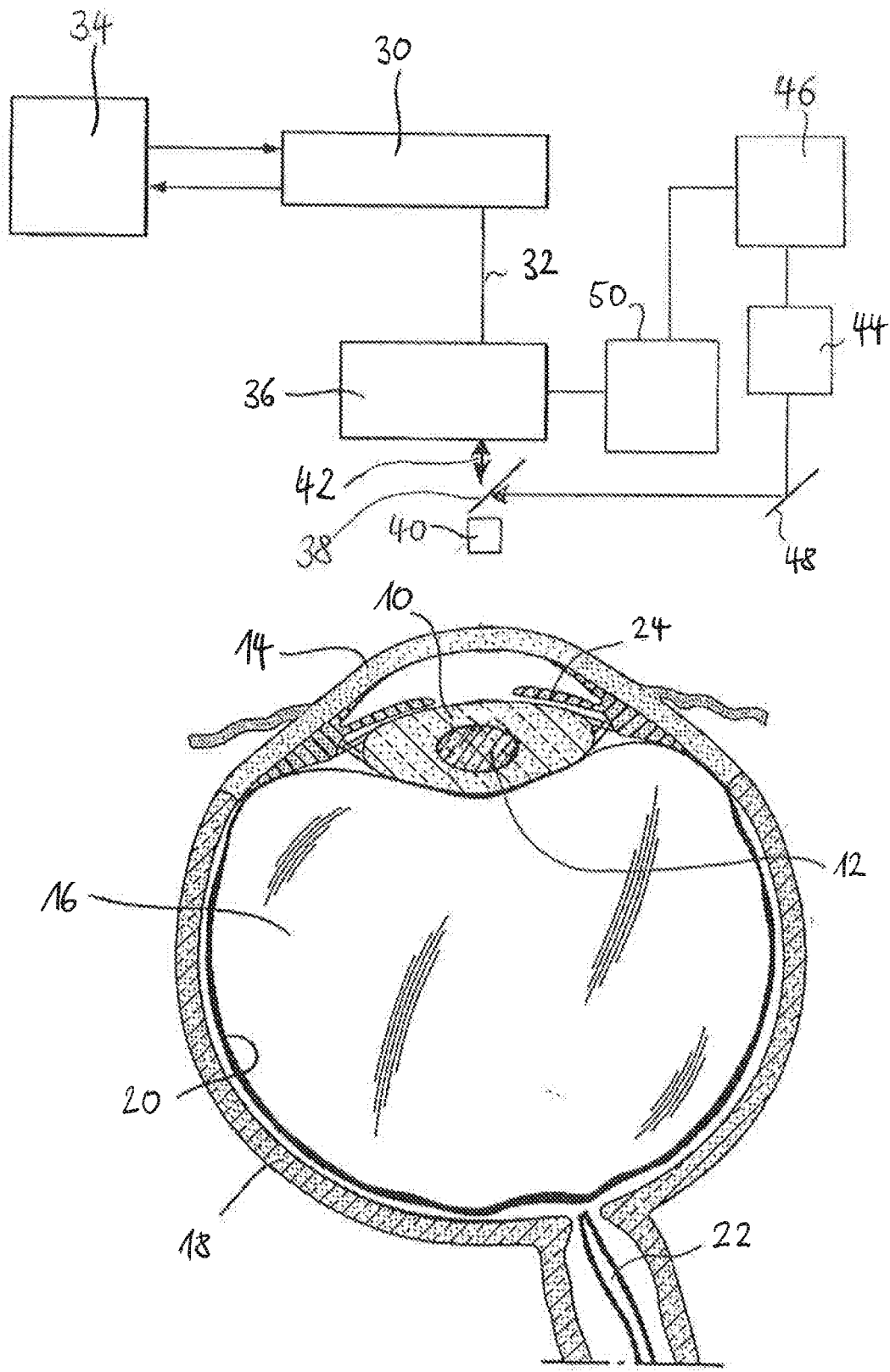

SYSTEM FOR FRAGMENTING AN EYE LENS NUCLEUS

FIELD

The invention relates to a system for fragmenting an eye lens nucleus in connection with a so-called cataract operation.

BACKGROUND OF THE INVENTION

A cataract operation consists of a plurality of steps, inter alia comminution of the content of the eye lens, in particular of the hard nucleus of the lens. There are no blood vessels in the human eye lens, and therefore, throughout life, metabolic products are deposited and concentrated in the lens nucleus. A protein paracrystal forms, which becomes harder with increasing age. In the prior art, in cataract surgery, the eye lens nucleus is shattered (fragmented) by means of an ultrasonic probe and the fragments are removed by suction. This procedure can take considerable time and is also a cause of possible complications.

Prior art

Recently, a new technique of so-called phacoemulsification has increasingly been used, namely photofragmentation and photocapsulorrhexis. A femtosecond laser (that is to say, a laser with pulse lengths in the femtosecond range) is thereby used on the one hand to allow a circular and defined opening to be made in the anterior lens capsule and on the other hand to fragment the lens nucleus into small pieces which then, in a similar manner as in the conventional technique mentioned above, can be removed so that a new intraocular lens can be inserted.

In photofragmentation using a femtosecond laser, fragmentation is carried out in the hard material of the eye lens nucleus.

BRIEF DESCRIPTION OF THE FIGURES

FIG. 1 shows, schematically, a system for fragmenting an eye lens nucleus.

DETAILED DESCRIPTION OF THE INVENTION

The object of the invention is to provide a system for fragmenting an eye lens nucleus, with which a cataract operation can be carried out more simply and with better results.

For this purpose, the invention teaches a system for fragmenting an eye lens nucleus, comprising: a first laser radiation source, configured to irradiate the eye lens nucleus with first radiation suitable for Brillouin spectroscopy; an apparatus for performing Brillouin spectroscopy with radiation scattered back by the eye lens nucleus in order to acquire Brillouin scattering measured data; a processing unit in or from which correlations between Brillouin scattering measured data and parameters of a second radiation suitable for fragmenting an eye lens nucleus are contained or derived; and a second laser radiation source having radiation guiding means, configured to irradiate the eye lens nucleus with the second radiation with the parameters correlated with the Brillouin scattering measured data of the irradiated eye lens nucleus for fragmenting the eye lens nucleus.

The invention is based on the finding that it is expedient for a cataract operation to adapt properties of the pulses of the femtosecond laser that are used for fragmentation to properties of the eye lens nucleus. Eye lens nuclei have different properties from patient to patient as regards their hardness and, generally, as regards their ability to be shattered with femtosecond laser pulses by microexplosions. Generally, the harder the eye lens nucleus, the greater the required energy density of the laser at the site of the microexplosion.

The invention is further based on the finding that so-called Brillouin spectroscopy is suitable for determining properties of the eye lens nucleus that are relevant here. Brillouin spectroscopy is concerned with an inelastic scattering of light at acoustic phonons. In the scattering of photons in the visible light range in crystals (thus here in the eye lens nucleus), there is an emission or absorption of phonons with very small frequency shifts in the scattered light. A distinction is made between Stokes shifts and anti-Stokes shifts. The techniques of Brillouin spectroscopy are widely developed as such, and this prior art can be used here.

With the system according to the invention, information about properties of the eye lens nucleus that are important for a subsequent surgical fragmentation of the nucleus can be obtained preoperatively by means of the apparatus for performing Brillouin spectroscopy ("Brillouin spectrometer"). In other words: the invention makes use of the finding that there is a correlation between results of Brillouin spectroscopy on the eye lens nucleus and parameters (properties) of the femtosecond laser pulses which lead to the best results as regards the fragmentation. In particular, this correlation can be established experimentally/empirically, for example by evaluating empirical surgical data and/or on the basis of comparative tests, etc.

Such empirically determined correlations between properties of the eye lens nucleus determined by Brillouin spectroscopy and parameters of the femtosecond laser pulses which yield optimal results for those properties of the eye lens nucleus (that is to say in the specific patient) can, for example, be stored in tabular form in a computer which belongs to the system. The parameter "eye lens hardness" can optionally be inserted into the correlation, that is to say information about the hardness of the eye lens nucleus is first derived from the Brillouin spectroscopy data, and the optimal set of parameters for the femtosecond pulses is derived from the hardness of the eye lens nucleus (again on the basis of empirically determined relationships in this respect).

There come into consideration as parameters of the femtosecond laser pulses in particular: pulse length, pulse frequency, pulse energy, pulse energy density, wavelength, and/or the pulse dimensions at the site of action in the eye lens nucleus.

Femtosecond laser pulses (here referred to as "second radiation") are guided into the eye lens nucleus in such a manner that they have their highest density at the desired site of the microexplosion. This can take place, for example, by means of strongly focusing optical means in such a manner that the focal point lies at the desired site of the microexplosion.

The femtosecond laser pulses are preferably projected onto the eye lens nucleus with a plurality of lines which are laterally offset (e.g. parallel) to one another, so that a plurality of adjacent cuts are produced in the eye lens nucleus in order to fragment it. The cuts are preferably applied cross-wise, that is to say substantially in a grid pattern. The pattern and/or the energy of the radiation is thereby preferably so adjusted in dependence on the hardness of the eye lens nucleus that, as the eye lens nucleus becomes harder, the spacing between the lines (thus also between the cuts) becomes larger and the energy per line (cut) likewise becomes greater compared to less hard eye lens nuclei. Empirically, this has been found to be advantageous. Here too, the correlation between the results of the Brillouin spectroscopy and the optimal configuration of the cutting lines is determined empirically and stored in the system for optimal use of the system in dependence on the properties of the eye lens nucleus of the patient.

On the other hand, however, the radiation guiding means can also have optical fibers which are configured to be pushed to the eye lens nucleus in order to trigger the microexplosion there.

The techniques of Brillouin spectroscopy on the one hand and the techniques of fragmentation with femtosecond laser pulses on the other hand are each known as such and can be used when carrying out the present invention.

The invention thus provides adaptation of the explosion energy in the microexplosions to the properties of the eye lens nucleus by means of adjustment of parameters of the femtosecond laser pulses, such as, for example, pulse energy/cutting width.

An exemplary embodiment of the invention is described in greater detail below with reference to FIG. 1.

FIG. 1 shows, schematically, a system for fragmenting an eye lens nucleus.

FIG. 1 shows an eye lens 10 with an eye lens nucleus 12, the cornea 14, vitreous body 16, sclera 18, retina 20, optic nerve 22 and iris 24.

A first radiation source 30 is used for Brillouin spectroscopy. It generates first laser radiation suitable for that purpose, typically in the visible range. A control device 34 controls the radiation source 30. The "first" radiation 32 of the radiation source 30 is directed onto and into the eye lens nucleus 12 by means known as such, and radiation scattered back by the eye lens nucleus 12 is measured with the Brillouin spectrometer 36. The double arrow 42 indicates the direction of the measuring radiation and the backscattered radiation.

The measured data of the Brillouin spectrometer 36 are inputted into a computer 50.

In the computer 50 there are stored, for example, data in tabular form relating to a correlation between the measured data of the Brillouin spectrometer 36 and parameters of femtosecond laser pulses, which data have been acquired empirically and which indicate, for measured data of the Brillouin spectrometer 36 determined for a specific patient, optimal parameters for femtosecond laser pulses, with which good fragmentation of the eye lens nucleus 12 is achieved.

Femtosecond laser pulses with those parameters are then generated by means of a second radiation source 44, that is to say a femtosecond laser, by the control device 46. The femtosecond laser pulses so generated are then so directed into the eye lens nucleus 12, via mirrors 38, 48, etc. shown schematically, that the highest radiation density for producing the mentioned microexplosions is present at desired locations therein. The mirrors 38, 48 and the radiation guiding means 40 are, for the sake of simplicity, shown the same for the first and the second radiation, but in practice optimal radiation guiding means for the first radiation and for the second radiation can be introduced into the beam path.

The control devices 34, 46 for the lasers 30 and 44, and the computer 50 can be integrated into a single processing unit.

REFERENCE NUMERALS USED IN FIG. 1

10 eye lens
12 eye lens nucleus
14 cornea
16 vitreous body
18 sclera
20 retina
22 optic nerve
24 iris
30 first radiation source
32 first radiation
34 control device (for 30)
36 Brillouin spectrometer
38 mirror
40 radiation guiding means
42 double arrow
44 second radiation source
46 control device (for 44)
48 mirror
50 processing unit
52 second radiation

The invention claimed is:

1. A system for fragmenting an eye lens nucleus by causing microexplosions to shatter the eye lens nucleus, the system comprising:
   a first laser radiation source, configured to irradiate the eye lens nucleus with first radiation suitable for Brillouin spectroscopy;
   an apparatus for performing Brillouin spectroscopy with radiation scattered back from the eye lens nucleus in order to acquire Brillouin scattering measured data;
   a processing unit configured to determine a hardness of the eye lens nucleus based on the Brillouin scattering measured data, and configured to obtain empirically or experimentally determined correlations between the determined hardness and parameters of a second radiation suitable for fragmenting the eye lens nucleus by causing microexplosions to shatter the eye lens nucleus, wherein the correlations yield optimal results for the determined hardness of the eye lens nucleus;
   a femtosecond laser having radiation guiding means, configured to irradiate the eye lens nucleus with the second radiation with the parameters correlated with the Brillouin scattering measured data of the irradiated eye lens nucleus, in order to fragment the eye lens nucleus by causing microexplosions to shatter the eye lens nucleus, and
   wherein the parameters of the second radiation are in particular one or more of the following: pulse length, pulse frequency, pulse energy, pulse energy density, wavelength, pulse dimensions at the site of action in the eye lens nucleus.

2. The system as claimed in claim 1, wherein the radiation guiding means are focusing optical means.

3. A system for fragmenting an eye lens nucleus by causing microexplosions to shatter the eye lens nucleus, the system comprising:
   a first laser radiation source, configured to irradiate the eye lens nucleus with first radiation suitable for Brillouin spectroscopy;
   an apparatus for performing Brillouin spectroscopy with radiation scattered back from the eye lens nucleus in order to acquire Brillouin scattering measured data;
   a processing unit configured to determine a hardness of the eye lens nucleus based on the Brillouin scattering measured data, and configured to obtain empirically or experimentally determined correlations between the determined hardness and parameters of a second radiation suitable for fragmenting the eye lens nucleus by causing microexplosions to shatter the eye lens nucleus, wherein the correlations yield optimal results for the determined hardness of the eye lens nucleus;

a femtosecond laser having radiation guiding means, configured to irradiate the eye lens nucleus with the second radiation with the parameters correlated with the Brillouin scattering measured data of the irradiated eye lens nucleus, in order to fragment the eye lens nucleus by causing microexplosions to shatter the eye lens nucleus, and wherein the radiation guiding means have optical fibers which are configured to be pushed to the eye lens nucleus.

4. A system for fragmenting an eye lens nucleus by causing microexplosions to shatter the eye lens nucleus, the system comprising:

a first laser radiation source, configured to irradiate the eye lens nucleus with first radiation suitable for Brillouin spectroscopy;

an apparatus for performing Brillouin spectroscopy with radiation scattered back from the eye lens nucleus in order to acquire Brillouin scattering measured data;

a processing unit configured to determine a hardness of the eye lens nucleus based on the Brillouin scattering measured data, and configured to obtain empirically or experimentally determined correlations between the determined hardness and parameters of a second radiation suitable for fragmenting the eye lens nucleus by causing microexplosions to shatter the eye lens nucleus, wherein the correlations yield optimal results for the determined hardness of the eye lens nucleus;

a femtosecond laser having radiation guiding means, configured to irradiate the eye lens nucleus with the second radiation with the parameters correlated with the Brillouin scattering measured data of the irradiated eye lens nucleus, in order to fragment the eye lens nucleus by causing microexplosions to shatter the eye lens nucleus, and wherein the second radiation is directed linearly in order to produce linear cuts on the eye lens nucleus, wherein the second radiation is directed at the eye lens nucleus in a pattern of a plurality of mutually offset lines, wherein a pattern of the mutually offset lines is grid-like, and wherein, as the hardness of the eye lens nucleus increases, a spacing of the mutually offset lines and an energy of the second radiation per line are increased compared with an eye lens nucleus of lower hardness.

* * * * *